United States Patent [19]

Mori et al.

[11] Patent Number: 5,053,552
[45] Date of Patent: Oct. 1, 1991

[54] PROCESS FOR PRODUCING α,β-UNSATURATED ALDEHYDE

[75] Inventors: Toshiki Mori, Kurashiki, Japan; Shigeaki Suzuki, Mountain View, Calif.; Takashi Onishi; Kazuo Yamamoto, both of Kurashiki, Japan

[73] Assignee: Kuraray Company, Ltd., Kurashiki, Japan

[21] Appl. No.: 537,617

[22] Filed: Jun. 14, 1990

[30] Foreign Application Priority Data

Aug. 11, 1989 [JP] Japan ................................ 1-208396

[51] Int. Cl.$^5$ ........................ C07C 45/45; C07C 45/00
[52] U.S. Cl. ..................................... 568/460; 568/426; 568/435; 568/459; 568/465; 568/484; 568/485
[58] Field of Search ............... 568/433, 435, 458, 459, 568/460, 484, 485, 496, 497, 483, 465

[56] References Cited

U.S. PATENT DOCUMENTS 3,862,235  1/1975  Himmele et al. .................. 568/460
4,560,790  12/1985  Ryu .................................... 568/460
4,739,111  4/1988  Ryu .................................... 568/460

OTHER PUBLICATIONS

Ringold et al., J. Amer. Chem. Soc., vol. 78, p. 816+ (1965).

Primary Examiner—Werren B. Lone
Attorney, Agent, or Firm—Oblon, Spivak, McClelland, Maier & Neustadt

[57] ABSTRACT

The present invention provides a novel process for producing α,β-unsaturated aldehydes including industrial important fragrances such as citral and sinensal, starting materials for preparing pharmaceutical drugs such as senecioaldehyde, farnesal, 8-acetoxy-2,6-dimethyl-2,6-octadienal and the like, directly and in high yield, from formic acid esters of allylic alcohols in the presence of a catalytic amount of aluminum alkoxide by the oxidation of the corresponding alehyde.

6 Claims, No Drawings

PROCESS FOR PRODUCING α,β-UNSATURATED ALDEHYDE

BACKGROUND OF THE INVENTION

1. Field of the Invention

This invention relates to a novel process for producing α, β-unsaturated aldehydes including industrial important fragrances such as citral and sinensal, starting materials for preparing pharmaceutical drugs such as senecioaldehyde, farnesal, and 8-acetoxy-2,6-dimethyl-2,6-octadienal, and the like.

Previously, there is generally known a process which comprises oxidizing allylic alcohols in the presence of an aluminum alkoxide catalyst to obtain the corresponding α, β-unsaturated aldehydes (refer to Organic Reactions, Vol. 6, Chapter 5, U.S. Pat. No. 4,663,488 (1987), and Japanese Patent Laid-open No. SHO 51 (1976)-141,801).

Also there is known a process which comprises reacting formic acid esters of secondary alcohols with cyclohexanone in large excess in the presence of aluminum alkoxide in a large amount under reflux by heating to obtain the corresponding ketones (refer to J. Am. Chem. Soc., Vol. 78, 816 (1956)).

2. Description of the Related Art

Formic acid esters of allylic alcohols can be readily prepared, for example, according to a process which comprises chlorination of double bond, or a process which comprises reacting sodium formate to allyl chlorides obtained by hydrochloric acid-addition reaction of a diene compound such as isoprene, myrcene, and the like (refer to Japanese Patent Laid-open No. SHO 63(1988)-227,546).

The process of preparing α, β-unsaturated aldehydes from formic acid esters of allylic alcohols comprises hydrolyzing the esters to the corresponding allylic type alcohols, and thereafter oxidizing the obtained allylic type alcohols. But this process has a long reaction sequence and therefore has been desired to be simplified.

Furthermore, the successful application of the well-known oxidizing process for formic acid esters in the presence of an aluminum alkoxide catalyst to prepare α, β-unsaturated aldehydes from formic acid esters of allylic type alcohols known as relatively high reactivity is difficult to obtain the objective α, β-unsaturated aldehydes in high yield because of the active side reactions including the self-condensation of produced α, β-unsaturated aldehydes etc. for its severe reaction conditions.

The object of the invention is to provide a process for producing α, β-unsaturated aldehydes, directly and in high yield, from readily available industrial starting materials such as formic acid esters of allylic type alcohols, dissolving the aforementioned problems.

SUMMARY OF THE INVENTION

According to the invention, the above object can be achieved by a process for producing α, β-unsaturated aldehydes of the general formula (I),

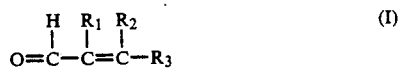

wherein $R_1$ and $R_2$ are independently a hydrogen atom or a lower alkyl group, and $R_3$ is a hydrogen atom, an alkyl group, an alkenyl group, an alkadienyl group or an alkatrienyl group without having a cumulative double bond, an aralkyl group, an aryl group with or without being substituted at the ring, a hetero-aromatic group; or the aforementioned alkyl group, alkenyl group, alkadienyl group or alkatrienyl group or the alkyl group of aralkyl group being mono-substituted by a lower alkanoyloxy group, an arylcarbonyloxy group, a lower alkoxy group or an aralkyloxy group with or without being substituted at a position on the ring: $R_1$ and $R_3$ integrated with their respectively bonding carbon atoms form a 1-cycloalkenyl group with or without being substituted, and $R_2$ has the same meaning as defined above: or $R_2$ and $R_3$ integrated with their respectively bonding carbon atoms form a cycloalkylidene group, and $R_1$ has the same meaning as defined above, comprising the reaction between formic acid esters of allylic type alcohols of the general formula (II),

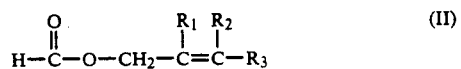

wherein $R_1$, $R_2$ and $R_3$ have the same meanings as defined above, and aldehydes of the general formula (III),

wherein $R_4$, $R_5$ and $R_6$ are independently a lower alkyl group, a lower alkenyl group, an allenyl group, an aryl group with or without being substituted at a position on the ring or a hetero-aromatic group; any two groups selected from $R_4$, $R_5$ and $R_6$ are integrated to form a lower alkylidene group or an alkylene group, and the other group has the same meaning as described above; or $R_4$, $R_5$ and $R_6$ are integrated with their respectively bonding carbon atoms to form a 1-cycloalkenyl group, an aryl group with or without being substituted with at a position on the ring, or a hetero-aromatic group: in the presence of an aluminum alkoxide in an catalytic amount.

DESCRIPTION OF THE PREFERRED EMBODIMENTS $R_1$, $R_2$, $R_3$, $R_4$, $R_5$ and $R_6$ in the above described formulas are described in detail.

$R_1$ and $R_2$ are independently a hydrogen atom or a lower alkyl group. Examples of a lower alkyl group include alkyl groups having from one to four carbon atoms, such as a methyl group, an ethyl groups, a n-propyl group, an i-propyl group, a n-butyl group, a sec-butyl group, a t-butyl group and the like. $R_3$ is a hydrogen atom, an alkyl group, an alkenyl group, an alkadienyl group or an alkatrienyl group without having a cumulative double bond, an aralkyl group with or without being substituted at a position of the ring, an aryl group with or without being substituted at a position of the ring or a hetero-aromatic group; or the aforementioned alkyl group, alkenyl group, alkadienyl group, alkatrienyl group or the alkyl group of aralkyl group being mono-substituted by a lower alkanoyloxy group, an arylcarbonyloxy group, a lower alkoxy group or an aralkyloxy group with or without being substituted at a position on the ring.

The carbon atom number of the alkyl group is not particularly limited, but usually from one to fifteen, preferably from one to four. Examples of the alkyl group include a methyl group, an ethyl group, a n-propyl group, an i-propyl group, a n-butyl group, a sec-butyl group, a t-butyl group and the like.

The carbon atom number of the alkenyl group is not particularly limited, but usually from two to fifteen, preferably from two to six. Examples of the alkenyl group include a vinyl group, an allyl group, a 1-propenyl group, a 4-methyl-3-pentenyl group and the like.

The carbon atom number of the alkadienyl group without having a cumulative double bond is not particularly limited but usually from five to twenty, preferably from six to eleven. Example of the alkadienyl group include a 3-methylene-4-pentenyl group, a 4,8-dimethyl-3,7-nonadienyl group and the like.

The carbon atom number of the alkatrienyl group without having a cumulative double bond is not particularly limited but usually from seven to thirty, preferably from twelve to twenty four. Examples of the alkatrienyl group include an 4,8,12-trimethyl-3,7,11-tridecatrienyl group and the like.

The aryl group is not particularly limited. Examples of the aryl group include a phenyl group and the like. For example, a phenyl group is substituted by one or two or more of substituents at any one of ortho-, meta- or para-position of the phenyl group. Examples of the substituents for the phenyl group include lower alkoxy group such as a methoxy group, a ethoxy group and the like; halogen atoms such as a chlorine atom, a bromine atom, a fluorine atom and an iodine atom; lower alkyl groups such as a methyl group, an ethyl group, a propyl group and the like.

There is no particular limitation for the aralkyl group with or without being substituted. Examples of the aralkyl group include a phenyl lower alkyl group with the alkyl group having usually from one to four cabon atoms, and with or without being substituted a position on the ring, like the aforementioned aryl group; such as a 2-phenylethyl group, a 2-phenylpropyl group, a 3-phenylpropyl group, a 3-p-tolylbutyl group and the like.

Examples of the hetero-aromatic compounds include a furyl group and the like.

As described above, the aforementioned alkyl group, alkenyl group, alkadienyl group or alkatrienyl group, or the alkyl group of the aralkyl group may be mono-substituted by a lower alkanoyloxy group, an arylcarbonyloxy group, a lower alkoxy group or an aralkyl group with or without being substituted at a position on the ring.

Many of the mono-substituent positions of the aforementioned alkyl group, alkenyl group, alkadienyl and alkatrienyl group are at a ω-positon, but may be at a mid position.

Examples of the substituents include lower alkanoyloxy groups having from one to four carbon atoms such as an acetoxy group, a propionyloxy group, a butylyloxy group and the like, and arylcarbonyloxy groups such as a benzoyloxy group, a p-tolyloxy group and the like.

Examples of the lower alkoxy groups as substituents include the ones having from one to four carbon atoms such as a methoxy group, an ethoxy group and the like.

Examples of the aralkyloxy group with or without substituted at a position on the ring include a benzyloxy group, a p-methoxybenzyloxy group and the like.

Also, $R_1$, $R_2$ and $R_3$ may be in that $R_1$ and $R_3$ integrated with their respectively bonding carbon atoms form a 1-cycloalkenyl group with or without being substituted and $R_2$ has the same meaning as defined above.

Examples of 1-cycloalkenyl group include the ones having from five to seven carbon atoms such as a 1-cyclopentenyl group, a 1-cyclohexenyl group, a 1-cycloheptenyl group and the like.

Examples of the substituents include a methyl group as being $R_2$ and/or a gem-dimethyl group bonding to any one of saturated carbon atom on the ring.

Further $R_1$, $R_2$ and $R_3$ may be in that $R_2$ and $R_3$ integrated with their respectively bonding carbon atoms form a cycloalkylidene group, and $R_1$ has the same meaning as above.

Examples of the cycloalkylidene group having from five to seven carbon atoms include a cyclopentylidene group, a cyclohexylidene group, a cycloheptylidene group and the like.

Examples of the formic acid esters of allylic alcohols include allyl formate, crotyl formate, prenyl formate, geranyl formate, neryl formate, farnesyl formate, geranylgeranyl formate, 8-acetoxy-2,6-dimethyl-1-formyloxy-2,6-octadiene, 8-benzyloxy-2,6-dimethyl-1-formyloxy-2,6-octadiene, 6-p-tolyl-2-methyl-1-formyloxy-2-heptene, 2-methyl-6-methylene-1-formyloxy-2,7-octadiene, 1-formyloxy-2-pentene, cinnamyl formate, 6,6-dimethyl-2-methyl-1-cyclohexene-1-yl-methyl formate, 3,3-dimethyl-1-cyclohexene-1-yl-methyl formate, 5,5-dimethyl-1-cyclohexene-1-yl-methyl formate, cyclohexylidenethyl formate.

$R_4$, $R_5$ and $R_6$ of the general formula (III) are independently a lower alkyl group, a lower alkenyl group, an aryl group with or without being substituted on a position of the ring or a hetero-aromatic group. Among these cases, the following cases are preferred: the case in which all of $R_4$, $R_5$ and $R_6$ are lower alkyl groups and the case in which one of $R_4$, $R_5$ and $R_6$ is a lower alkenyl group, an allenyl group, an aryl group with or without being substituted on a position of the ring or a hetero-aromatic group, and another two are lower alkyl groups.

Examples of the lower alkyl groups include the ones having from one to six carbon atoms, preferably from one to five carbon atoms such as a methyl group, an ethyl group, a n-propyl group, an i-propyl group, a t-butyl group, an i-amyl group and the like.

Examples of the lower alkenyl groups include the ones having from two to six carbon atoms such as a vinyl group, an allyl group, 1-propenyl group, a 4-methyl-3-pentenyl group and the like.

Examples of the aryl group with or without being substituted at a position on the ring include a phenyl group, a phenyl group being substituted by one or two or more of substituents which are selected from the group consisting of lower alkoxy groups such as a methoxy group and the like, halogen atoms such as a chlorine atom, a bromine atom, a fluorine atom and an iodine atom, lower alkyl groups such as a methyl group, an ethyl group, a propyl group and the like, at any one of ortho-, meta- or para-position of the ring, and the like.

Examples of the hetero-aromatic group include a furyl group and the like.

Any two groups selected from $R_4$, $R_5$ and $R_6$ may be integrated to form a lower alkylidene group or a lower alkylene group, and the other group has the same meaning as described above.

Examples of the lower alkylidene groups include the ones having from one to six carbon atoms, preferably from one to four carbon atoms such as a methylidene group and the like.

Examples of the lower alkylene groups include the ones having from four to six carbon atoms such as a tetramethylene group, a pentamethylene group and the like.

The remaining one group of $R_4$, $R_5$ or $R_6$ that is not integrated may be any group as described above and generally is a lower alkyl group.

$R_4$, $R_5$ and $R_6$ integrated with their respectively bonding carbon atoms can form a 1-cycloalkenyl group, an aryl group with or without being substituted at a position on the ring or a hetero-aromatic group.

Examples of the 1-cycloalkenyl group include the ones having from five to seven carbon atoms such as a 1-cyclopentenyl group, a cyclohexenyl group and the like.

Examples of the aryl group with or without being substituted at a position on the ring include a phenyl group, a phenyl group substituted by one or two or more of substituents which are selected from the group consisting of lower alkoxy groups such as a methoxy group and the like, halogen atoms such as a chlorine atom, a bromine atom, a fluorine atom, and an iodine atom, lower alkyl groups such as a methyl group, an ethyl group, a propyl group and the like at any one of ortho-, meta- or para-position of the ring, and the like.

Examples of the hetero-aromatic group include a furyl group, particularly 2-furyl group and the like.

Examples of the aldehyde of the general formula (III) include trimethylacetaldehyde, 2,2-dimethyl-4-pentenal, 2,2-dimethylpentane-3,4-dienal, 1-methylcyclohexane-1-carboaldehyde, 2-phenylpropane-2-carboaldehyde, 3-methyl-2-methylene-1-butanal, 1-cyclohexene-1-carboaldehyde, benzaldehyde, tolualdehyde, mesitaldehyde, p-methoxybenzaldehyde, p-chlorobenzaldehyde, m-chlorobenzaldehyde, furfural and the like.

The amount of the aldehyde of the general formula (III) used in the reaction is generally in an amount of one or more equivalents, preferably from 1.1 to 3 equivalents, for an efficient reaction carrying out to the amount of the formic acid ester of allylic alcohol to be oxidized.

Examples of the aluminum alkoxide catalyst used for the reaction include the ones generally used for the Oppenauer oxidation reaction of alcohol, such as aluminum isopropoxide, aluminum t-butoxide, aluminum s-butoxide, aluminum phenoxide and the like. Among these, aluminum isopropoxide is preferable because of the availability.

The amount of the aluminum catalyst used in the reaction is in the range of from 0.1 to 30 mole percent, preferably from 2 to 10 mole percent to the amount of formic acid ester of allylic alcohol.

The temperature of the reaction depending on the reaction period is in the range of from 10° C. to 180° C. However, the preferred temperature of the reaction is in the range of from 20° C. to 50° C. considering the stability of produced $\alpha$, $\beta$-unsaturated aldehydes.

The use of a solvent is not essential for the reaction but may be used in the difficulty of the aluminum alkoxide catalyst dissolution.

Examples of the solvent include hydrocarbons such as toluene, hexane and the like, chlorinated hydrocarbons such as methylene chloride, chloroform and the like, ethers such as tetrahydrofuran, diethyl ether and the like, esters such as ethyl acetate and the like.

The reaction period depending on the amount of the catalyst used and the reaction temperature is in the range of from 30 minutes to 5 hours.

The reaction is quenched by the addition of water, hydrochloric acid, sulfuric acid and the like to the reaction system. After the completion of the reaction, the objective $\alpha$, $\beta$-unsaturated aldehyde is separated and purified from the reaction mixture according to the following manner.

After the extraction of the reaction mixture by the use of an organic solvent selected from the group consisting of toluene, hexane, diethyl ether, methylene chloride, ethyl acetate and the like, the organic layer is separated, washed successively with water and an aqueous solution of sodium carbonate, distilled off the solvent from the solution, and subjected to distillation or column-chromatography for purification.

Further, after quenching the reaction by the addition of a small amount of water, the reaction mixture may be subjected to distillation as such without separation of the organic layer to obtain the objective $\alpha$, $\beta$-unsaturated aldehyde.

EXAMPLES

The present invention is more particularly described by way of examples, which should not be construed as limiting the present invention.

EXAMPLE 1

Preparation of Citral from Geranyl Formate by Using Trimethylacetaldehyde

A dried 100 ml flask was charged and mixed with 18.2 g (100 mmol) of geranyl formate, 17.3 g (200 mmol) of trimethylacetaldehyde, and 642 mg (3 mmol) of aluminum isopropoxide in an atmosphere of nitrogen, followed by agitation at 40° C. for 3 hours.

To the reaction mixture was added 20 ml of 1N hydrochloric acid and 30 ml of toluene, and phase-separated. The resultant organic phase was washed twice with 20 ml of 1N hydrochloric acid respectively, and further washed with 20 ml of water and separated, and washed with 5% sodium carbonate aqueous solution, thereafter distilled off the organic solvent under a reduced pressure, followed by distillation (at a boiling point of 68° C. at 0.3 mmHg) to obtain 13.68 g of citral (at a yield of 90%).

EXAMPLE 2

Preparation of Citral from Furfural by Using Geranyl Formate

According to the same procedure of Example 1, using 19.5 g (200 mmol) of furfural, and 642 mg (3 mmol) of aluminum isopropoxide, 18.2 g (100 mmol) of geranyl formate was oxidized to obtain citral at a yield of 86%.

EXAMPLE 3

Preparation of 8-acetoxy-2,6-dimethyl-2,6-octadienal from 8-acetoxy-2,6-dimethyl-1-formyloxy-2,6-octadiene Using trimethylacetaldehyde A dried 500 ml flask was charged and mixed with 170.5 g (purity 70.4%, 500 mmol) of 8-acetoxy-2,6- dimethyl-1-formyloxy-2,6-octadiene, 86.9 g (1 mol) of trimethyl acetaldehyde, 3.06 g (15 mmol) of aluminum isopropoxide in an atmosphere of nitrogen, followed by agitation at 40° C. for 2 hours.

After the quenching of reaction by the addition of 2 ml of water, unreacted trimethyl acetaldehyde and by products of formic acid ester of neopentyl alcohol were distilled off under a reduced pressure.

From the residue, the objective 8-acetoxy-2,6-octadienal was obtained by distillation under reduced pressure (boiling point: 120° C. at 1 mmHg) in a yield of 89%.

EXAMPLE 4

Preparation of 8-acetoxy-2,6-dimethyl-2,6-octadienal from 8-acetoxy-2,6-dimethyl-1-formyloxy-2,6-octadiene Using 2,2-dimethyl-1-pentenal According to the same procedure of Example 3, using 102.3 g (purity 70.7%, 300 mmol) of 8-acetoxy-2,6-dimethyl-1-pentenal, and 1.84 g (90 mmol) of aluminum isopropoxide, 8-acetoxy-2,6-dimethyl-2,6-octadienal was obtained in a yield of 90.9%.

EXAMPLES 5 to 8

According to the same procedure of Example 1, from the following formic acid esters of allylic alcohols, the α, β-unsaturated aldehydes were obtained in the yields as described below.

EXAMPLE 5

Formic Acid Ester of Allylic Alcohol

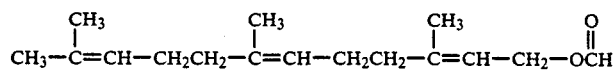

Product

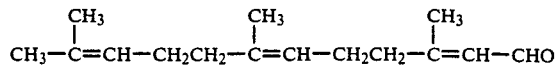

Yield: 90%

EXAMPLE 6

Formic Acid Ester of Allylic Alcohol

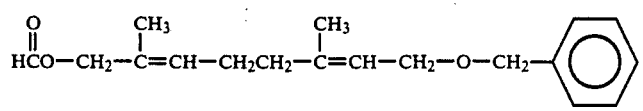

Product

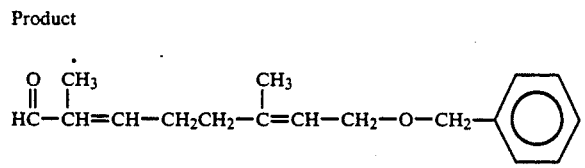

Yield: 85%

EXAMPLE 7

Formic Acid Ester of Allylic Alcohol

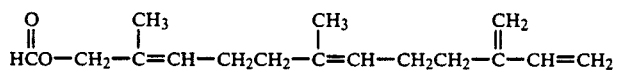

Product

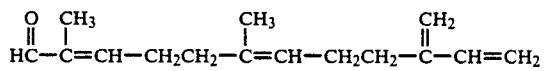

Yield: 82%

EXAMPLE 8

Formic Acid Ester of Allylic Alcohol

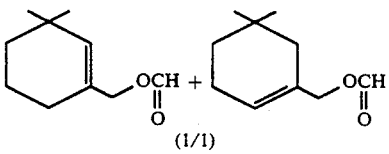

Product

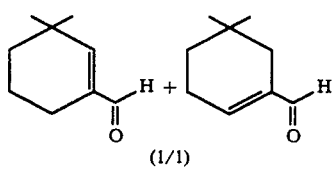

Yield: 81%

What is claimed is:

1. A process for producing an α, β-unsaturated aldehyde of the formula

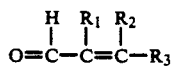 (I)

wherein $R_1$ and $R_2$ are independently a hydrogen atom or a lower alkyl group, and $R_3$ is a hydrogen atom, an alkyl group, an alkenyl group, an alkadienyl group or an alkatrienyl group without having a cumulative double bond, an aralkyl group, an aryl group with or without being substituted at the ring, or a hetero-aromatic group; or the aforementioned alkyl group, alkenyl group, alkadienyl group or alkatrienyl group or the alkyl group of the aralkyl group being mono-substituted by a lower alkanoyloxy group, an arylcarbonyloxy group, a lower alkoxy group or an aralkyloxy group with or without being substituted at a position on the ring; $R_1$ and $R_3$ integrated with their respectively bonding carbon atoms form a 1-cycloalkenyl group with or without being substituted, and $R_2$ has the same meaning as defined above; or $R_2$ and $R_3$ integrated with their respectively bonding carbon atoms form a cycloalkylidene group, and $R_1$ has the same meaning as defined above, comprising the reaction at a temperature in the range of from 10° C. to 120° C. between a formic acid ester of an allylic type alcohol of the formula (II),

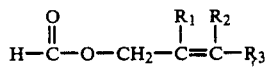 (II)

wherein $R_1$, $R_2$ and $R_3$ have the same meanings as defined above, and an aldehyde of the formula (III),

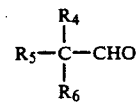 (III)

wherein $R_4$, $R_5$ and $R_6$ are independently a lower alkyl group, a lower alkenyl group, an allenyl group, an aryl group with or without being substituted at a position on the ring or a hetero-aromatic group; any two groups selected from $R_4$, $R_5$ and $R_6$ are integrated to form a lower alkylidene group or an alkylene group, and the other group has the same meaning as described above; or $R_4$, $R_5$ and $R_6$ are integrated with their respectively bonding carbon atoms to form a 1-cycloalkenyl group, an aryl group with or without being substituted at a position on the ring, or a heterocyclic aromatic group; in the presence of an aluminum alkoxide in a catalytic amount.

2. A process according to claim 1, wherein the aldehyde of the formula (III) is used in an amount of one or more equivalents to the amount of the formic acid ester of allylic alcohol of the formula (II).

3. A process according to claim 2, wherein the aldehyde of the formula (III) is used in an amount of from 1.1 to 3 equivalents to the amount of the formic acid ester of allylic alcohol of the formula (II).

4. A process according to claim 1, wherein the aluminum alkoxide is used in an amount of from 0.1 to 30 mole percent to the amount of the formic acid ester of allylic alcohol of the formula (II).

5. A process according to claim 1, wherein the aluminum alkoxide is used in an amount of from 2 to 10 mole percent to the amount of the formic acid ester of allylic alcohol of the formula (II).

6. A process according to claim 1, wherein the reaction is carried out at a temperature in the range of from 20° C. to 50° C.

* * * * *